US006849763B2

(12) United States Patent
Dolitzky et al.

(10) Patent No.: US 6,849,763 B2
(45) Date of Patent: Feb. 1, 2005

(54) PROCESS FOR PREPARING RAC-BICALUTAMIDE AND ITS INTERMEDIATES

(75) Inventors: Ben-Zion Dolitzky, Petach Tikva (IL); Ofer Reany, Lower Gallilee (IL); Jenny Shammai, Kiryat Yam (IL)

(73) Assignee: Biogal Gyógyszergyár Rt., Debrecen (HU)

( * ) Notice: Subject to any disclaimer, the term of this patent is extended or adjusted under 35 U.S.C. 154(b) by 0 days.

(21) Appl. No.: 10/796,822

(22) Filed: Mar. 8, 2004

(65) Prior Publication Data

US 2004/0176638 A1 Sep. 9, 2004

Related U.S. Application Data

(62) Division of application No. 10/170,721, filed on Jun. 13, 2002, now Pat. No. 6,737,550.
(60) Provisional application No. 60/371,069, filed on Apr. 9, 2002, and provisional application No. 60/298,009, filed on Jun. 13, 2001.

(51) Int. Cl.$^7$ ........................ C07L 53/122; C07L 53/134
(52) U.S. Cl. ......................................................... 562/520
(58) Field of Search ............................................ 562/520

(56) References Cited

U.S. PATENT DOCUMENTS

| | | |
|---|---|---|
| 3,254,094 A | 5/1966 | Ross |
| 4,554,381 A | 11/1985 | Desbois |
| 4,636,505 A | 1/1987 | Tucker |
| 5,723,485 A | 3/1998 | Gungor et al. |
| 6,160,011 A | 12/2000 | Miller et al. |
| 6,184,249 B1 | 2/2001 | Sovak et al. |
| 6,291,504 B1 | 9/2001 | Nugiel et al. |
| 6,306,874 B1 | 10/2001 | Fraley et al. |
| 6,358,985 B1 | 3/2002 | Anthony et al. |

FOREIGN PATENT DOCUMENTS

| | | |
|---|---|---|
| WO | WO 93/19770 | 10/1993 |
| WO | WO 01/00608 | 1/2001 |
| WO | 01/34563 A1 * | 5/2001 |

OTHER PUBLICATIONS

MacPeek, Donald L. et al., "Synthesis of Glycidic Esters by Epoxidation of α,β–Unsaturated Esters With Peracetic Acid," J. Am. Chem., 1959, vol. 81, pp. 680–683.

Emmons, William D. et al., "Peroxytrifluoroacetic Acid. IV. The EpoXidation of Olefins," J. Am. Chem., 1955, vol. 77, pp. 89–92.

Ho, Winston et al., "Alkylglycidic Acids: Potential New Hypoglycemic Agents," J. Med. Chem., 1986, vol. 29, pp. 2184–2190.

Lieberman, Herbert A. et al., *Pharmaceutical Dosage Forms: Tablets*, vol. 2, 2$^{nd}$ Ed., Marcel Dekker, Inc. New York (1990), pp. 107–200.

Database CAPLUS on STN, Chemical Abstracts, CA: 129:244921, Freskos et al., "Preparation of aromatic sulfonyl alpha–hydroxy hydroxamic acid compounds as matrix metalloprotease inhibitors".

Database CAPLUS on STN, Chemical Abstracts, CA:128:75188, Takahashi et al., "Preparation and formulation of aryl sulfides, sulfoxides, and sulfones as matrix metalloproteinase inhibitors".

Database CAPLUS on STN, Chemical Abstracts, CA: 136:12767, Slusarek et al., "Color photographic thermally processable film comprising blocked developer compound".

Database CAPLUS on STN, Chemical Abstracts, CA: 86:171116, Buettner et al., "Trifluoromethyl–substituted aminobenzonitriles".

Database CAPLUS on STN, Chemical Abstracts, CA: 108: 150026, Tucker et al., "Resolution of the non–steriodal antiandrogen 4'–cyano–3–(4–fluorophenylsulfonyl)–2–hydroxy–2–methyl–3'–(trifluoromethyl) propionanilide and the determination of the absolute configuration of the active enantiomer".

Database CAPLUS of STN, Chemical Abstracts, CA: 2002:414656, James et al., "A two–step synthesis of the anti–cancer drug (r,S)–bicalutamide".

Database CAPLUS on STN, Chemical Abstracts, CA:120:191513, Horchler von Locquenghien et al., "Preparation of oxiranecarboxylates and analogs".

Database CAPLUS on STN, Chemical Abstracts, CA:89:90113, Rastetter, et al. "3,5–Dinitroperoxybenzoic acid. A crystalline, storable substitute for peroxytrifluoroacetic acid".

Database CAPLUS on STN, Chemical Abstracts, CA:134:326279, Ekwuribe, et al. Asymmetric synthesis and antiandrogenic use of enantiomers of Casodex (bicalutamide) and derivaives from enantiomers of citramalic acid or proline.

* cited by examiner

Primary Examiner—Taofiq Solola
(74) Attorney, Agent, or Firm—Kenyon & Kenyon

(57) ABSTRACT

The present invention relates to a new process for the synthesis of racemic and optically active bicalutamide starting from ethyl pyruvate and methyl methacrylate. The present invention discloses processes of preparing bicalutamide intermediates including ethyl-[2-{4-fluorophenyl sulfone)]-2-hydroxy propionate, 1,2-epoxy-2-methyl propionate and 2-hydrox-2-methyl-3-(4-fluorophenylthio) propionic acid. The present invention further discloses micronized rac-bicalutamide and the preparation thereof.

9 Claims, 2 Drawing Sheets

PROCESS FOR PREPARING RAC-BICALUTAMIDE AND ITS INTERMEDIATES

CROSS REFERENCE TO RELATED APPLICATIONS

This application is a division of U.S. patent application Ser. No. 10/170,721 filed Jun. 13, 2002, now U.S. Pat. No. 6,737,550, which claims the benefits under 35 U.S.C. §119 (e) of Provisional application Ser. Nos. 60/298,009, filed Jun. 13, 2001 and 60/371,069, fled on Apr. 9, 2002, the disclosure of which are incorporated herein by reference in their entireties.

FIELD OF THE INVENTION

The present invention relates to process for preparing rac-bicalutamide and its intermediates. The prevent invention also relates to micronized rac-bicalutamides and their preparations thereof.

BACKGROUND OF THE INVENTION

Bicalutamide is also known as N-[4-cyano-3-trifluoromethyl-phenyl]-3-[4-fluorophenyl-sulfonyl]-2-hydroxy-2-methyl-propionamide and has the following chemical formula.

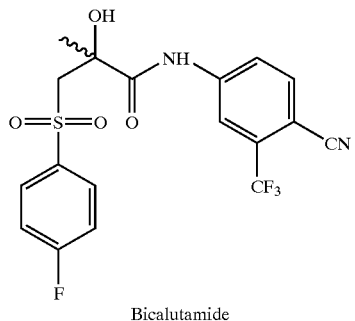

Bicalutamide

Bicalutamide is an acylanilid that has anti-androgen activity. It is known to selectively decrease the testosterone level without influencing the regulation mechanisms of the hypothalamus.

The international patent No. WO 93/19770 describes both R-(−) enantiomer and S-(+) enantiomer for bicalutamide, of which the R-(−) isomer is reported to be more active and possesses lesser side-effects (e.g., headache, gynecomistia and giddiness) when used in therapy treatment.

U.S. Pat. No. 4,636,505 describes processes for preparing acylanilides.

The international Pat. No. WO 01/00608 describes a process for racemic and optically pure N-[4-cyano-3-trifluoromethylphenyl]-3-[4-fluorophenyl-sulfonyl]-2-hydroxy-2-methyl-propionamide. The process involves multiple steps including at least reacting with thionyl choride; hydrolyzing under aqueous basic conditions; sulfonylating with sulfonyl halogenide; and oxidizing with inorganic peroxy salt, or m-chloroperbenzoic acid (MCPBA) or aqueous hydrogen peroxide. However, the synthetic pathways involve the use of substrates (such as sodium hydride) that are dangerously explosive in nature.

There is a constant need to improve the synthesis process for bicalutamide which are economical and environmental safe and feasible.

We have now found a simpler method of preparing bicalutamide and its intermediates without using dangerous oxidizing compounds such as m-chloroperbenzoic acid.

OBJECTS AND SUMMARY OF THE INVENTION

The present invention provides new synthetic pathways for preparing rac-bicalutamide and its intermediates.

According to one object, the present invention is directed to a rac-bicalutamide intermediate having a chemical formula of [X], which represents a stable organo lithium salt of 4-fluorophenyl methyl sulfone.

According to another object, the present invention is directed to a process of preparing [X]; comprising the step of reacting 4-fluorophenyl methyl sulfone with butyl lithium to form the organo lithium salt of 4-fluorophenyl methyl sulfone.

According to another object, the present invention provides a novel process for preparing rac-ethyl 1-[2-{4-fluorophenyl sulfone}]-2-hydroxy propionic acid, comprising the step of reacting the organo lithium salt of 4-fluorophenyl methyl sulfone with ethyl pyruvate.

According to another object, the present invention is directed to a rac-bicalutamide intermediate having a chemical formula of [Y], which represents a stable lithium salt of 5-amino-2-cyano-benzotrifluoride.

According to another object, the present invention provides a precess for preparing [Y], comprising the step of reacting 5-amino-2-cyano-benzotrifluoride with butyl lithium to form the lithium salt of 5-amino-cyano-benzotrifluoride.

According to another object, the present invention provides a process for preparing rac-bicalutamide, comprising the step of reacting [Y] with rac-ethyl 1-[2-{4-fluorophenyl sulfone}]-2-hydroxy propionic acid.

According to another object, the present invention provides a process for preparing rac-ethyl-[2-{4-fluorophenyl sulfone}]-2-hydroxy propionic acid, comprising the steps of:

1) mixing 4-fluorophenyl methyl sulfone with butyl lithium to obtain an intermediate having a chemical structure [X];
2) adding ethyl pyruvate; and
3) recovering rac-ethyl-[2-{4-fluorophenyl sulfone}]-2-hydroxy propionic acid.

Preferably, 1,4 diazabicyclo[2.2.2]octane in tetrahydrofuran is used as a stablizied agent in step 1.

According to another object, the present invention provides a process for preparign rac-bicalutamide comprising the steps of:

1) mixing 5-amino-2-cyano-benzotrifluoride and butyl lithium to obtain a lithium salt of 5-amino-2-cyano-benzotrifloride;
2) adding rac-ethyl-[2-4-fluorophenyl sulfone}]-2-hydroxy propionic acid; and
3) recovering rac-bicalutamide.

Preferably, the step 1) is occurred in the presence of 1,4 diazabicyclo[2.2.2]octane in tetrahydrofuran.

According to one object, the present invention provides a novel process of preparing micronized forms of rac-bicalutamide.

According to another object, the present invention provides a synthesis process of preparing rac-bicalutamide with a particle size in which the mean particle size enhances the rate of dissolution and the reproducibility of dissolution. The present invention provides rac-bicalutamide in which the mean particle size imparts an improved and stable dissolution profile.

According to another object, the present invention provides rac-bicalutamide formulations containing rac-bicalutamide having relatively small particles, and corresponding large surface area.

According to another object, the present invention provides rac-bicalutamide with a particle size which enhances the rate of dissolution and the reproducibility of the rate of dissolution.

According to another object, the present invention provides rac-bicalutamide in which the mean particle size imparts an improved and stable dissolution profile.

According to another object, the present invention provides rac-bicalutamide and formulations containing rac-bicalutamide having a mean particle diameter of less than 200 μm.

According to another object, the present invention provides a process for preparing micronized rac-bicalutamide.

According to another object, the present invention provides pharmaceutical compositions comprising micronized rac-bicalutamide.

DETAILED DESCRIPTION OF THE INVENTION

Definitions

As used herein, rac-bicalutamide refers to both the R-(−) enantiomer and S-(+) enantiomer of bicalutamide. Rac-bicalutamide is the racemic and optically pure R-(−) and S-(+) isomers of N-[4-cyano-3-trifluoromethyl-phenyl]-3-[4-fluorophenyl-sulfonyl]-2-hydroxy-2-methyl-propionamide. It is to be understood that this invention encompasses the racemic form of bicalutamide and any optically-active form which possesses anti-androgenic activity. It is a matter of common general knowledge how a racemic compound may be resolved into its optically-active forms and how any anti-androgenic activity present in any of these forms may be determined. One skilled in the art will appreciate that the separation of optical isomers can be achieved by conventional resolution; such as fractional crystallization or flash-chromatography.

As used herein, the term "micronized" refers to particles having a mean particle diameter of less than about 200 μm.

As used herein, the term "μm" refers to "micrometer" which is $1 \times 10^{-6}$ meter.

The following abbreviations are used herein: DCM is dichloromethane. THF is tetrahydrofuran. DABCO is 1,4 dizazbicyl [2.2.2] octane. ACB is 5-amino-2-cyano-benzotrofluoride. BCL is rac-bicalutamide. 4-FPMS is 4-fluorophenyl methyl sulfone.

The present invention provides a novel process for preparing rac-bicalutamide from ethyl pyruvate and 4-fluoropheynl methyl sulfone via the formation of an intermediate with chemical formula of [X].

The present invention further provides a novel process for preparing rac-bicalutamide from 4-fluorophenyl methyl sulfone. Butyl lithium reacts with 4-fluorophenyl methyl sulfone with a base to form an organo lithium the intermediate (i.e., with chemical formula of [X]), optionally in the presence of anion stabilizer such as DABCO. The base refers to strong bases such as lithium diisopropyl amid (LDA) or its derivatives. This reaction is preferably carried out in an inert organic solvent, for example tetrahydrofuran or diethyl ether. Most preferable solvent is tetrahydrofuran. The reaction is preferably carried out at a low temperature, for example −40° C. to 10° C. Most preferable temperature is between −2° C. and 2° C.

Figure 1:
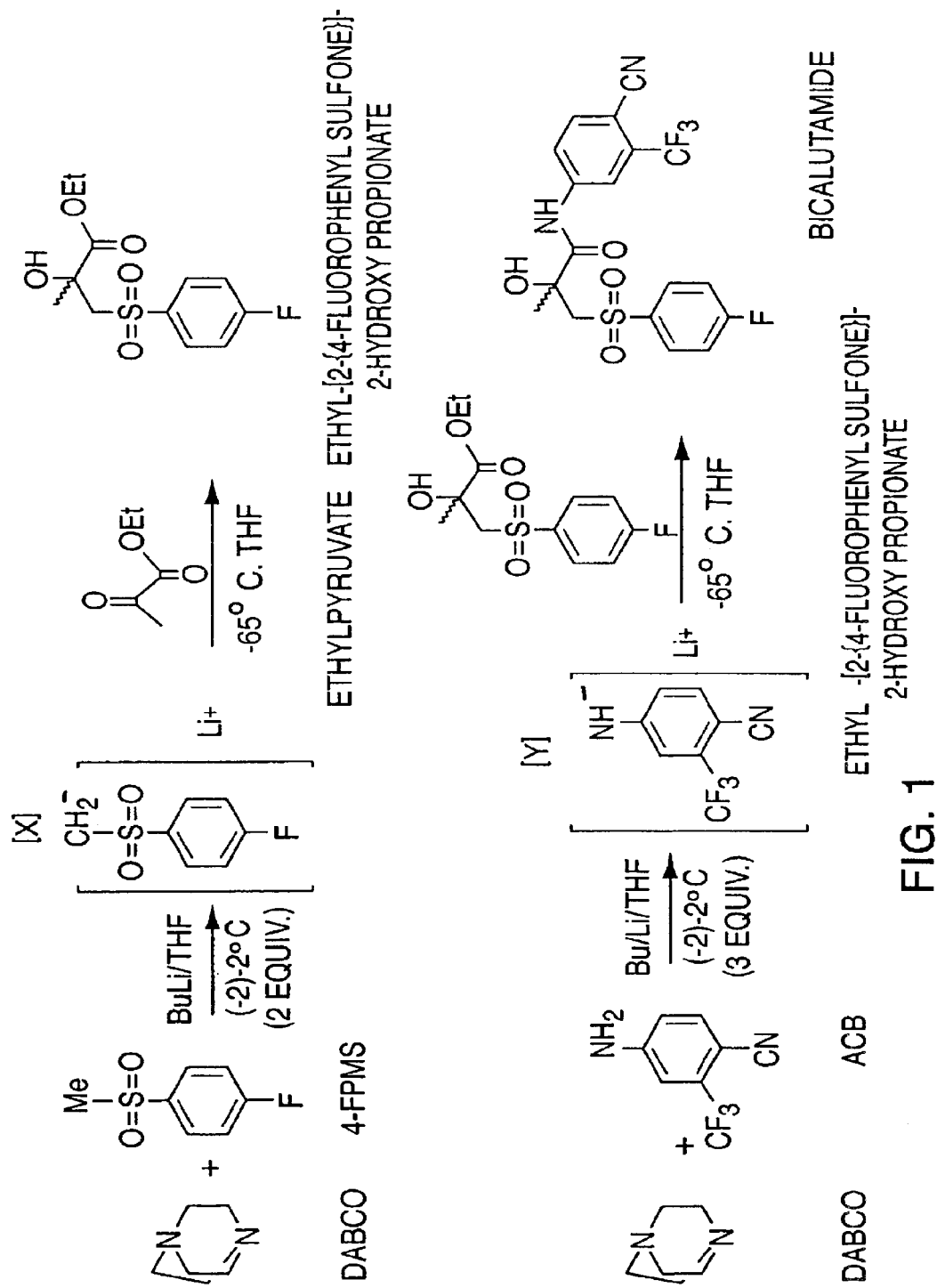
FIG. 1 depicts the reaction pathway of rac-bicalutamide synthesis starting from ethyl pyruvate.

FIG. 1 illustrates the schematic process for preparing rac-bicalutamide from ethyl pyruvate and 4-fluorophenyl methyl sulfone. The intermediate with general chemical formula of [X] reacts with ethyl pyruvate to form ethyl-[2-4-{4-fluorophenyl sulfone}]-2-hydroxy propionate. This reaction is preferably carried out in an inert organic solvent, for example tetrahydrofuran or diethyl ether. Most preferable solvent is tetrahydrofuran. The reaction is preferably carried out at a low temperature, for example −60° C. to −100° C. Most preferable temperature is −60° C.

The present invention provides a process of preparing rac-bicalutamide from 5-amino-2-cyano-benzotrifluoride. Butyl lithium reacts with 5-amino-2-cyano-benzotriflouride with a base to form an organo lithium the intermediate (i.e., with chemical formula of [Y]), optionally in the presence of anion stabilizer such as DABCO. The base refers to strong bases such as lithium diisopropyl amid (LDA) or its derivatives. This reaction is preferably carried out in an inert organic solvent, for example tetrahydrofuran or diethyl ether. Most preferable solvent is tetrahydrofuran. The reaction is preferably carried out at a low temperature, for example −40° C. to 10° C. Most preferable temperature is between −2° C. and 2° C.

The present invention provides a process of preparing rac-bicalutamide from 5-amino-2-cyano-benzotrifluoride via intermediate with chemical formula of [Y]. Intermediate with chemcial formula [Y] thus formed reacts with rac-ethyl-[2-{4-fluorophenyl sulfone}]-2-hydroxy propionate to form rac-bicalutamide. This reaction is preferably carried out in an inert organic solvent, for example tetrahydrofuran or diethyl ether. Most preferable solvent is tetrahydrofuran. The reaction is preferably carried out at a low temperature, for example −60° C. to −100° C. Most preferable temperature is −60° C.

The detailed procedures of preparing rac-ethyl-[2-{4-fluorophenyl sulfone}]-2-hydroxy propionic acid from ethyl pyruvate and 4-fluorophenyl methyl sulfone as well as rac-bicalutamide from rac-ethyl-[2-{4-fluorophenyl sulfone}]-2-hydroxy propionic acid and 5-amino-2-cyano-benzotrifluoride are illustrated in FIG. 1.

The process according to our invention is described in detail by the following, but not limiting, examples.

EXAMPLE 1

Preparation of rac-Ethyl-[2-{4-Fluorophenyl Sulfone}]-2-Hydroxy Propionate

4-Fluorophenyl methyl sulfone (4-FPMS) (5 grams, 27.8 mmol) and 1,4 diazabicyclo[2.2.2]octane (DABCO) (3.2 grams, 28.5 mmol) were dissolved in tetrahydrofuran (THF) and cooled in dry-ice acetone bath to about −2° C.

A 2.5 M solution of butyl lithium in hexanes (14.5 mL, 36.2 mmol) was added to the cold THF solution dropwise via a syringe while keeping the temperature between about −2° C. to about 2° C. After addition was completed the stirring was continued for about 1 hour while maintaining the temperature at about −2° C. Then, the temperature was lowered to about −65° C. and a solution of ethyl pyruvate (3.67 grams, 31.6 mmol) in THF (30 mL) was added dropwise.

After addition was completed, the stirring was continued for an hour at temperatures between about 65° C. and about −30° C. and then followed by an addition of 2N HCl (30 mL)

dropwise to the reaction mixture at about −30° C. The reaction was allowed to warm-up to room temperature and the mixture was evaporated in vacuo on a rotary evaporator to remove THF and ethanol.

The residual material was extracted with diethyl ether (3×100 mL). The combined ether extracts were dried over $Na_2SO_4$, filtered and the filtrate was completely evaporated to give a crude oil.

The product was purified by column chromatography on silica gel via eluting with dichloromethane (DCM) to give rac-ethyl-[2-{4-fluorophenyl sulfone}]-2-hydroxy propionate as colorless oil.

The purified product was characterized by a $^1H$ NMR (500 MHz, $CDCl_3$): 7.92 (m, 2H), 7.22 (m, 2H), 4.29 (m, 2H, $OCH_2$), 3.77 (d,J=15 Hz,1H, $CH_{2\alpha}$), 3.68 (bs, 1H, OH), 3.55 (d, J=15 Hz, 1H, $CH_{2\beta}$), 1.45 (s, 3H, Me), 1.35 (t, J=7 Hz, 3H, $OCH_2CH_3$).

The purified product was further characterized by a $^{13}C$ NMR (125.7 MHz, $CDCl_3$): 174.7 ppm ($CO_{ester}$), 166.4 (C-4', $J_{C-F}$=258 Hz), 137.5 ((c-1'), 131.7 (C-2',6', $J_{C-F}$=9 Hz), 117.0 (C-3',5', $J_{C-F}$=21.6 Hz), 72.9 ($C_{quat}$), 64.6 ($CH_2$), 63.6 ($OCH_2$), 27.9 ($CH_3$), 14.7 ($OCH_2CH_3$).

The purified product was further characterized by HPLC (acetonitrile:water 1:1 with 0.01% TFA): 5.4 mins.

EXAMPLE 2

Preparation of rac-N-[4-Cyano-3-Trifluoromethyl-Phenyl]-3-[4-Fluorophenyl Sulfonyl]-2-Hydroxy-2-Methyl-Propionamide 5-Amino-2-cyano-benzotrifluoride (ACB) (0.27 grams, 1.45 mmol) and 1,4diazabicyclo[2.2.2]octane (DABCO) (0.32 grams, 2.85 mmol) were dissolved in tetrahydrofuran (THF) (30 mL) and cooled in dry-ice acetone bath to about −2° C.

A 2.5M solution of butyl lithium in hexanes (2 mL, 5 mmol) was added to the cold THF solution dropwise via a syringe while keeping the temperature between about −2 to about 2° C. After addition was completed, the stirring was continued for 1 hour while maintaining the temperature at about −2° C. The temperature was then lowered to about −65° C. and a solution of rac-Ethyl-[2-{4-fluorophenyl sulfone}]-2-hydroxy propionate (0.34 grams, 1.17 mmol) in THF (20 mL) was added dropwise.

After addition was completed, the stirring was continued for an hour at temperatures between about −65° C. and about −30° C. after which 2N HCl (30 mL) was added dropwise to the reaction mixture at about −30° C. The reaction was allowed to warm-up to room temperature and the mixture was evaporated in vacuo on a rotary evaporator to remove THF and ethanol.

The residual material was extracted with diethyl ether (3×100 mL). The combined ether extracts were dried over $Na_2SO_4$, filtered and the filtrate was completely evaporated to give a crude oil.

The product was purified by column chromatography on silica gel eluting with ethyl acetate—petroleum ether to give rac-N-[4-cyano-3-trifluoromethyl-phenyl]-3-[4-fluorophenyl sulfonyl]-2-hydroxy-2-methyl-propionamide in about 40% yield, as a pale yellow solid.

Figure 2:
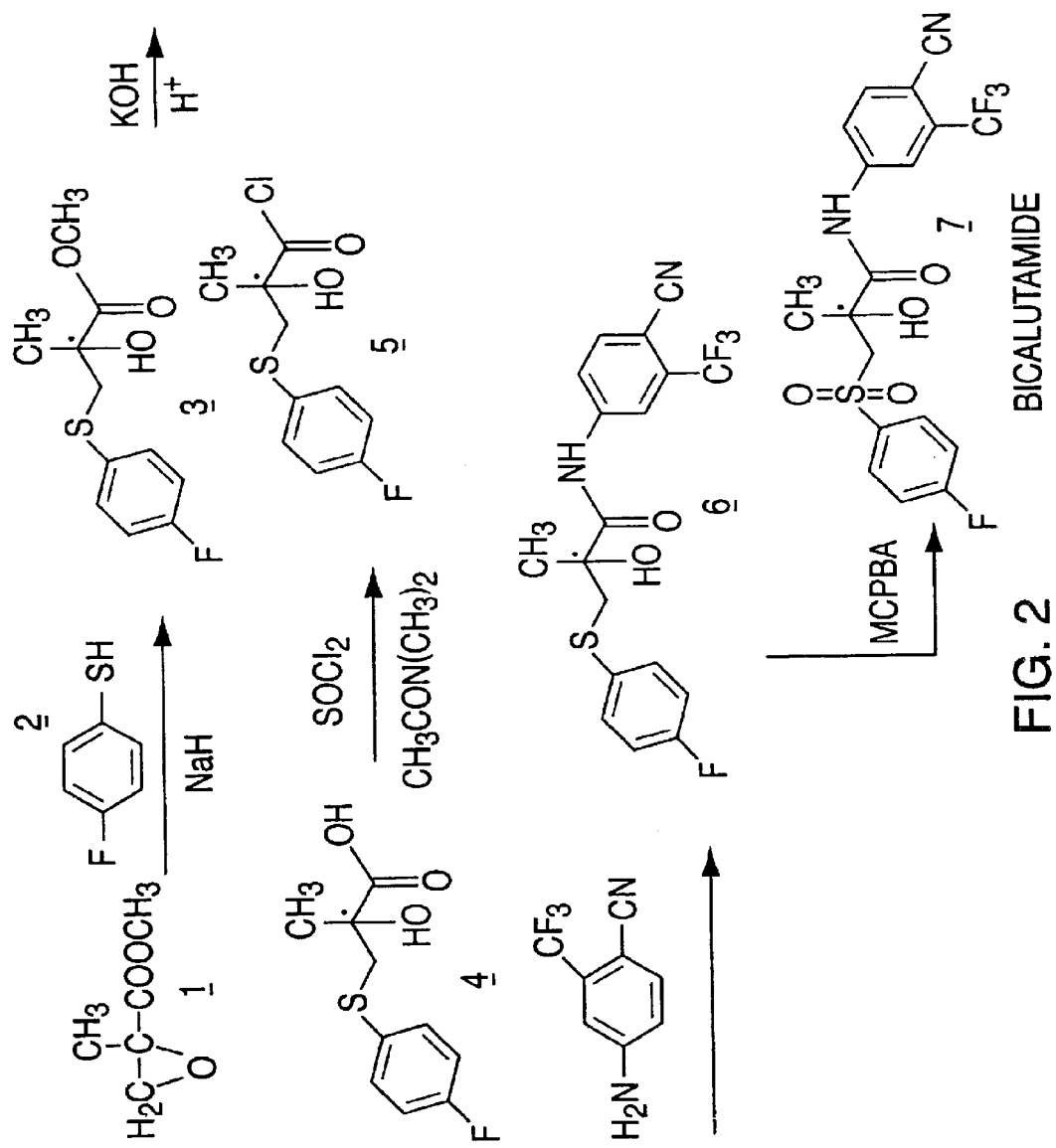
FIG. 2 depicts the reaction pathway of rac-bicalutamide synthesis starting from methyl methacrylate.

The present invention further provides a novel process for preparing rac-bicalutamide from methyl methacrylate. FIG. 2 illustrates the schematic process for preparing rac-bicalutamide from methyl methacrylate.

According to FIG. 2, the starting material was methyl methacrylate, which can usually be converted into the epoxide only under harsh conditions (i.e. with peracetic acid in ethyl acetate at 75° C. [J. A. Chem., 81, 680 (1959)], or with 90% hydrogen peroxide-trifluoroacetic anhydride at 40° C. [J. Am. Chem., 77, 89 (1955)], or with MCPBA in dichloromethane at 0° C. in low yield [J. Med. Chem., 29, 2184 (1986)]. The epoxidation under these conditions can be explosive. The present invention describes this oxidation using Oxone®.

The methyl 2-methyl-oxirane-carboxylate of formula (1), which was obtained by epoxidation, was reacted with 4-fluorothiophenol [formula (2)] in the presence of sodium hydride under the conditions listed in Scheme-2. The obtained methyl 2-hydroxy-2-methyl-3-(4-fluorophenylthio)-propionate of formula (3) was hydrolyzed with potassium hydroxide in aqueous ethanol over a period of 22 hours to yield the 2-hydroxy-2-methyl-3-(4-fluorophenylthio)-propionic acid of formula (4), which was converted into the acid chloride of formula (5) with thionyl chloride in dimethyl acetamide at −15° C.

The obtained acid chloride was reacted with 4-amino-2-trifluoromethyl-benzonitrile in dimethylacetamide at −15° C. to yield the thioether derivative of formula (6). The oxidation of the thioether derivative was carried out by known method with m-chloroperbenzoic acid in dichloromethane to yield the final product, bicalutamide, of formula (7).

The process according to our invention is described in detail by the following, but not limiting, examples.

EXAMPLE 3

Preparation of Methyl 1,2-Epoxy-2-Methyl-Propionate

In a 3L four-neck round bottom flask, Oxone® (50% $KHSO_5$, 227 grams, 0.75 mol) was dissolved in water (IL) and 10 M KOH was added to adjust the pH to~6 (~53 mL). Then, methyl methacrylate (13 mL, 0.122 mol) in methanol was added (50 mL) followed by 360 mL of water.

The solution was stirred at room temperature and the pH was continuously adjusted to pH=6 with 1M KOH (~270 mL). After 6 hr the reaction was stirred over night. Then, 2N HCl was added (100 mL, pH=3) and the entire aqueous solution was extracted with DCM (3×150 mL) for each 400 mL reaction solution. The combined DCM extracts were washed with saturated sodium sulfite solution followed by saturated sodium bicarbonate solution.

After drying and filtartion, DCM was removed by evaporation and the unreacted methyl methacrylate was distilled out. The residue contained the product as an oily material.

GC: (>97%, 1.45 min); yield: 66%; $^1H$ NMR (500 MHz, $CDCL_3$; □ ppm 3.72 (s,3H, Me), 3.07 (dd, J=6 Hz,, J=16 Hz, 1H, $H_\square$), 2.73 (d, J=6 Hz, 1H, $H_\square$), 1.55 (s, Me); $^{13}C$-NMR (125.7 MHz, $CDCL_3$; □ ppm): 172 ($CO_{ester}$), 54.3 ($CH_2$), 53.6 ($C_{quat}$), 53.2 ($Me_{ester}$), 18 (Me).

EXAMPLE 4

Preparation of 2-Hydroxy-2-Methyl-3-(4-Fluorophenylthio) Propionic Acid

To a solution of 4-fluorothiophenol (1 mL) in MeOH (32 mL) was added dropwise 2N $NaOH_{aq}$ (16 mL) under $N_2$, while the temperature was kept at 25° C. during the addition period. When addition was completed, the reaction mixture was stirred at room temperature for a further 90 min.

A solution of methyl-1,2-epoxy-2-methyl propionate (1.2 gram) in MeOH (20 mL) was then added dropwise at room temperature. When addition was completed, the reaction mixture was stirred over night at ambient temperature. To the reaction mixture 2N HCl (20 mL) was added followed by ethyl acetate (60 mL). The organic phase was separated. The aqueous phase (pH~2) was extracted with 60 mL of chloroform and then discarded. The ethyl acetate and chloroform extracts were combined.

After drying (MgSO$_4$) and filtration, the two organic solvents were evaoprated to leave an oily product which solidified upon standing at room temperature.

Purity: 75% (according to GC); Yield: 66%. GCMS: 230 m/z (13%); M.p.: 69.1–72.7° C.; $^1$H NMR (500 MHz, CDCL$_3$; □ ppm 7.43 (m, 2H, H-2',6'), 6.96 (m, 2H, H-3',5'), 3.39 (d, J=14 Hz, 1H, H$_□$), 3.17 (d, J=14 Hz, 1H, H$_□$), 1.53 (s, Me); $^{13}$C-NMR (125.7 MHz, CDCL$_3$; □ ppm): 180.4 (CO$_{acid}$), 162.6 (d, J$_{C-F}$=248 Hz, C-4'), 134.3 (d, J$_{C-F}$=7.5 Hz, C-2',6'), 130.8 (d, J$_{C-F}$=3.2 Hz, C-1'), 116.5 (d, J$_{C-F}$= 21.6 Hz, C-3',5'), 75.2 (C$_{quat}$), 53.3 (M$_{ester}$), 46.4 (CH$_2$), 26.0 (Me).

MICRONIZED RAC-BICALUTAMIDE

The Particle Size Distribution (PSD) of rac-bicalutamide may be used to determine the available surface area for the drug dissolution. Often, it is observed that the available surface area for drug dissolution correlates to both (a) the rate of dissolution and solubility where a great surface area enhances the solubility of a drug; and (b) enhances the rate of dissolution of a drug. The rate of dissolution of a drug effects the drug's bioavailability. Thus, the PSD of rac-bicalutamide, and in particular, the meagm particle diameter, are important parameters to characterize and predict the bioavailibility of rac-bicalutamide.

The present invention provides rac-bicalutamide formulations containing rac-bicalutamide having relative small particles and corresponding relatively large surface area.

The present invention provides rac-bicalutamide formulations continaing rac-bicalutamide having a mean particle diameter of less than 200 µm, preferably the mean particle diameter is less than 100 µm, more preferably the mean particle diameter is less than 20 µm, and most preferably the mean particle size is about 10 µm.

The present invention provides rac-bicalutamide having a mean particle diameter of between about 200 µm and about 10 µm. In one embodiment of the invention, rac-bicalutamide has a mean diameter of about 4.2 µm, more preferabley a mean diameter of 4.0 µm.

The present invention also provides process for preparing micronized rac-bicalutamide. By the methods of the present invention, rac-bicalutamide, which is prepared by methods known in the art, is separated by sieves to produce rac-bicalutamide wherein 50% has a mean particle diameter of below about 250 µm and about 80% has a mean particle diameter of below about 500 µm. The sieved rac-bicalutamide is then micronized by methods known in the art, e.g., in a micronizer, to yield rac-bicalutamide wherein 100% of rac-bicalutamide has a mean particle size of less than about 45 µm, preferably 99% of the rac-bicalutamide has a mean particle size of less than about 45 µm, more preferably, 93% of the rac-bicalutamide has a mean particle size of less than about 7.5 µm, more preferably the rac-bicalutamide isolated has a mean particle diameter of less than about 10 µm.

Micronized particles of rac-bicalutamide can be obtained by the use of conventional micronizing techniques after sieving to provide rac-bicalutamide wherein about 50% has a particle size of less than about 250 µm and about 80% has a particle size of less than 500 µm. By the methods of the present invention, the rac-bicalutamide where about 50% has a particle size less than 500 µm and about 80% has a particle size below about 500 µm, is micronized to the desired particle size range by methods known in the art, for example, using a ball mill, ultraonic means, fluid energy attrition mills, or using a jet mill, or other suitable means as disclosed in *Pharmaceutical Dosage Forms*: Tablets, Vol. 2, 2$^{nd}$ Ed., Lieberman et al. Ed., Marcel Dekker, Inc. New York (1990) p. 107–200, the content of which is incorporated by reference herein.

The present invention provides micronized rac-bicalutamide as pharmaceutical compositions that are particularly useful for its anti-androgen activity. Such compositions comprise micronized rac-bicalutamide with pharmaceutically acceptable carriers and/or excipients known to one of skilled in the art.

Preferably, these compositions are prepared as medicaments to be administered orally or intravenously. Suitable forms for oral administration niclude tablets, compressed or coated pills, dragees, sachets, hard or gelatin capsules, sub-lingual tablets, syrups and suspensions. While one of ordinary skill in the art will understand that dosages will vary according to the indication, age and severity of the disease of the patent etc., generally micronized rac-bicalutamide of the present invention will be administered at a daily dosage of about 2 mg to about 200 mg per day, and preferably about 5 mg to about 100 mg per day.

What is claimed is:

1. A process of preparing 2-hydroxy-2-methyl-3-(4-fluorophenylthio) propionic acid, comprising the steps of:
   a) preparing a solution of 4-fluorothiophenol in methanol;
   b) adding methyl-1,2-epoxy-2-methyl propionate to form a mixture;
   c) adding ethyl acetate to the mixture; and
   d) recovering 2-hydroxy-2-methyl-3-(4-fluorophenylthio) propionic acid.

2. The process according to claim 1, wherein the preparation of 4-fluorothiophenol solution is performed by adding a basic solution under N$_2$ flow.

3. The process according to claim 2, wherien the basic solution is selected from the group consisting of sodium hydroxide and potassium hydroxide.

4. The process according to claim 3, wherein the sodium hydroxide has a concentration of 2 N.

5. The process according to claim 1, wherein the mixture is formed by stirring.

6. The process according to claim 5, wherein the stirring is performed at room temperature for 90 minutes.

7. The process according to claim 1, wherein the recovering step is extraction.

8. The process according to claim 7, wherein the extraction is achieved by chloroform.

9. The process according to claim 1, wherein the recovering step further involves solidifying 2-hydrox-2-methyl-3-(4-fluorophenylthio) propionic acid.

* * * * *

UNITED STATES PATENT AND TRADEMARK OFFICE
CERTIFICATE OF CORRECTION

PATENT NO.           : 6,849,763 B2
APPLICATION NO.  : 10/796822
DATED                     : February 1, 2005
INVENTOR(S)          : Ben-Zion Dolitzky et al.

It is certified that error appears in the above-identified patent and that said Letters Patent is hereby corrected as shown below:

Title Page;
On the face of the patent, # (56) OTHER PUBLICATIONS, change "EpoXidation" to --Epoxidation--

On the face of the patent, #(56) OTHER PUBLICATIONS, change "non-steriodal" to --non-steroidal --

On the face of the patent, # (56) OTHER PUBLICATIONS, change "derivaives" to --derivatives--

Column 1, line 39, change "acylanilid" to --acylanilide--

Column 1, line 47, change "possesses" to --possess--

Column 1, line 47, change "gynecomistia" to --gynecomastia--

Column 1, line 59, change "choride" to --chloride--

Column 1, line 63, change "environmental" to --environmentally--

Column 2, line 26, change "precess" to --process--

Column 2, line 46, change "stablizied" to --stabilized--

Column 2, line 48, change "preparign" to --preparing--

Column 3, line 52, change "dizazbicyl" to --diazabicyclo--

Column 3, line 53, change "benzotrofluoride" to -- benzotrifluoride --

Column 3, line 57, change "fluoropheynl" to --fluorophenyl--

Column 3, line 62, change "lithium the intermediate" to -- lithium intermediate--

Column 3, line 65, change "amid" to --amide--

Column 4, line 17, change "benzotriflouride" to -- benzotrifluoride --

Column 4, line 18, change "lithium the intermediate" to -- lithium intermediate--

UNITED STATES PATENT AND TRADEMARK OFFICE
CERTIFICATE OF CORRECTION

PATENT NO. : 6,849,763 B2
APPLICATION NO. : 10/796822
DATED : February 1, 2005
INVENTOR(S) : Ben-Zion Dolitzky et al.

It is certified that error appears in the above-identified patent and that said Letters Patent is hereby corrected as shown below:

Column 4, line 31, change "chemcial" to --chemical--

Column 4, line 56, change "hexanes" to --hexane--

Column 6, line 47, change "filtartion" to --filtration--

Column 7, line 7, change "evaoprated" to --evaporated--

Column 7, line 28, change "effects" to --affects--

Column 7, line 29, change "meagn" to --mean--

Column 7, line 31, change "bioavailibility" to --bioavailability--

Column 7, line 36, change "continaing" to --containing--

Column 7, line 45, change "preferabley" to --preferably--

Column 8, line 10, change "ultraonic" to --ultrasonic--

Column 8, line 23, change "niclude" to --include--

Column 8, line 28, change "patent" to --patient--

Column 8, line 45, change "wherien" to --wherein--

Signed and Sealed this

Twenty-seventh Day of November, 2007

JON W. DUDAS
*Director of the United States Patent and Trademark Office*